(12) United States Patent
Tsukahara et al.

(10) Patent No.: US 8,016,989 B2
(45) Date of Patent: Sep. 13, 2011

(54) EXHAUST GAS SENSOR

(75) Inventors: Koju Tsukahara, Shizuoka-ken (JP);
Shigeyuki Ozawa, Shizuoka-ken (JP);
Isao Nonaka, Shizuoka-ken (JP)

(73) Assignee: Yamaha Hatsudoki Kabushiki Kaisha, Shizuoka (JP)

( * ) Notice: Subject to any disclaimer, the term of this patent is extended or adjusted under 35 U.S.C. 154(b) by 963 days.

(21) Appl. No.: 11/211,414

(22) Filed: Aug. 25, 2005

(65) Prior Publication Data

US 2006/0042946 A1   Mar. 2, 2006

(30) Foreign Application Priority Data

Aug. 25, 2004   (JP) ................................. 2004-244612

(51) Int. Cl.
*G01N 27/407* (2006.01)
(52) U.S. Cl. ........................ 204/428; 204/424
(58) Field of Classification Search .................. 73/23.32, 73/114.71, 114.72, 114.73
See application file for complete search history.

(56) References Cited

U.S. PATENT DOCUMENTS

| | | | |
|---|---|---|---|
| 5,246,562 A * | 9/1993 | Weyl et al. ..................... 204/424 |
| 5,271,477 A | 12/1993 | Gekka et al. |
| 5,271,480 A | 12/1993 | Takegami |
| 5,271,821 A * | 12/1993 | Ogasawara et al. ........... 204/429 |
| 5,360,081 A | 11/1994 | Takegami |
| 5,408,872 A | 4/1995 | Nonaka |
| 5,425,232 A | 6/1995 | Holtermann |
| 5,579,745 A | 12/1996 | Katoh et al. |
| 5,584,281 A | 12/1996 | Katoh |
| 5,637,792 A | 6/1997 | Kimura et al. |
| 5,694,909 A | 12/1997 | Kato |
| 5,697,353 A | 12/1997 | Katoh et al. |
| 5,702,276 A | 12/1997 | Nakase et al. |
| 5,711,148 A | 1/1998 | Katoh |
| 5,712,422 A | 1/1998 | Kato |
| 5,911,609 A | 6/1999 | Fujimoto et al. |
| 6,214,186 B1 * | 4/2001 | Watanabe et al. ............. 204/428 |
| 6,354,134 B1 * | 3/2002 | Katafuchi et al. ........... 73/23.32 |
| 6,505,466 B1 * | 1/2003 | Nagafusa et al. ............... 60/298 |
| 6,780,298 B2 | 8/2004 | Nakamura et al. |
| 2002/0195339 A1 * | 12/2002 | Nakamura et al. ............. 204/428 |

FOREIGN PATENT DOCUMENTS

| | | |
|---|---|---|
| DE | 44 36 580 A1 | 4/1996 |
| DE | 196 28 423 A1 | 9/1997 |
| JP | 09-280033 | 10/1997 |
| JP | 11013569 | 1/1999 |

* cited by examiner

*Primary Examiner* — Kaj K Olsen
*Assistant Examiner* — Kourtney R Salzman
(74) *Attorney, Agent, or Firm* — Keating & Bennett, LLP

(57) ABSTRACT

An exhaust gas sensor inhibits a detecting part of an exhaust gas sensor from being exposed to water and has high detection accuracy and high durability. The exhaust gas sensor has a sensor body and a protective cover. The sensor body has an outer housing. The outer housing has a plurality of gas inlets. A gas detection element for detecting a component of the exhaust gas (e.g., oxygen) disposed within the outer housing. The protective cover has a cylindrical shape and has a plurality of protrusions at its opposing ends. The protrusions provide a tight fit with the outer housing. The protective cover is attached to the outer periphery of the outer housing without closing gas inlets formed through the outer cylinder by press-fitting the outer cylinder into the protective cover.

22 Claims, 9 Drawing Sheets

EXHAUST GAS SENSOR

PRIORITY INFORMATION

The present application is based on and claims priority under 35 U.S.C. §119(a-d) to Japanese Patent Application No. 2004-244612, filed on Aug. 25, 2004, the entire content of which is expressly incorporated by reference herein.

BACKGROUND OF THE INVENTION

1. Field of the Invention

The present invention relates to exhaust gas sensors and, more particularly, to exhaust gas sensors that are mounted to an exhaust conduit of an exhaust system.

2. Description of the Related Art

Internal combustion engines typically power vehicles. Internal combustion engines output exhaust gases that contain combustion by-products. These exhaust gases often pass through an exhaust system before being expelled from the vehicle. Detectors often measure the concentration of oxygen in the exhaust gases so that the air-fuel ratio of the air-fuel mixture can be controlled based on an output from the detector. Typically, a detector is provided in an exhaust gas pipe of the exhaust gas system.

Personal watercraft or small planing boats often employ these detectors for measuring the concentration of oxygen in their exhaust gases. When used in these environments, the detector can be exposed to water as water can flow upstream (i.e., towards the internal combustion engine of the vehicle) through an exhaust gas pipe when, for example, the vehicle is turned over. Japanese Patent Publication No. Hei 11-13569 discloses an exhaust gas sensor designed to prevent a portion of the exhaust gas sensor from being exposed to water in the exhaust system.

Such exhaust gas sensors are often constructed by forming a chamber in the vicinity of an upper portion of a cylinder in the engine. The detecting component of the exhaust gas sensor protrudes in the upper section of the chamber. The chamber is typically in communication with the cylinder via an exhaust gas guide passage. An exhaust gas guide passage is connected to the bottom of the chamber at a position that is higher than the position where the cylinder is connected to the exhaust gas guide passage. The chamber is positioned away from the downstream portion of the exhaust gas pipe while the exhaust gas sensor is disposed at an upper position in the chamber. Thus, when water flows through the exhaust gas pipe towards the engine, the water may not reach the exhaust gas sensor. Also, since the exhaust gas guide passage is connected to the bottom of the chamber, even if water enters the chamber, it may be immediately discharged therefrom. Unfortunately, water can still reach the vicinity of the detecting part of the exhaust gas sensor. When the detecting part of the exhaust gas sensor gets wet with water, the accuracy of the exhaust gas sensor can be reduced, or the exhaust gas sensor can be damaged.

SUMMARY OF THE INVENTION

An aspect of the present invention includes an exhaust gas sensor which prevents a detecting sensor of the exhaust gas sensor from being exposed to water for high detection accuracy and high durability.

In some aspects, an exhaust gas sensor for an exhaust system comprises a gas detection element that is configured to detect an amount of a substance in a gas. An outer housing has a plurality of gas inlets. The gas inlets provide fluid communication through the outer housing. A protective cover covers and surrounds the outer housing. The gas detection element is positioned within the outer housing.

In other aspects, an exhaust system for a watercraft has an engine that comprises an exhaust conduit. The exhaust conduit has an exhaust gas passage through which exhaust gases discharged from the engine pass. An exhaust sensor of the exhaust system comprises a gas detection assembly disposed in the exhaust gas passage. The gas detection assembly comprises a gas detection element that is configured to detect an amount of a substance in exhaust gases. An outer housing surrounds the gas detection element and has at least one gas inlet. The at least one gas inlet provides fluid communication through the outer housing. A protective cover surrounds the outer housing.

In yet another aspect, an exhaust gas sensor for an exhaust system comprises a gas detection element configured to detect an amount of a substance in a gas. An outer housing has at least one fluid passage therethrough. The gas detection element is disposed within the outer housing. A protective cover is disposed so as to shield the at least one fluid passage of the outer housing.

BRIEF DESCRIPTION OF THE DRAWINGS

The above-mentioned and other features of the inventions disclosed herein are described below with reference to the drawings of preferred embodiments. The illustrated embodiments are intended to illustrate, but not to limit the inventions. The drawings contain the following Figures.

DETAILED DESCRIPTION OF THE PREFERRED EMBODIMENTS

Figure 1:
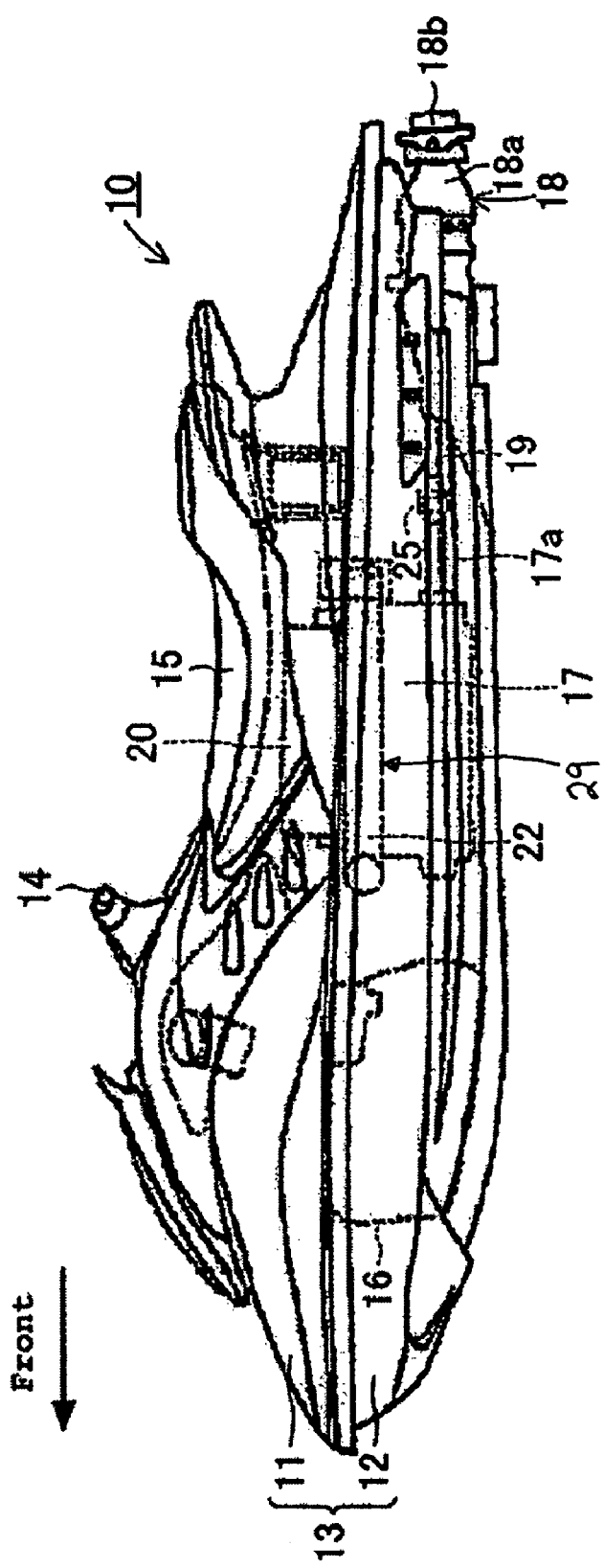
FIG. 1 is a partial cross-sectional, side elevation view of a watercraft having an exhaust system in accordance with an embodiment.
Figure 2:
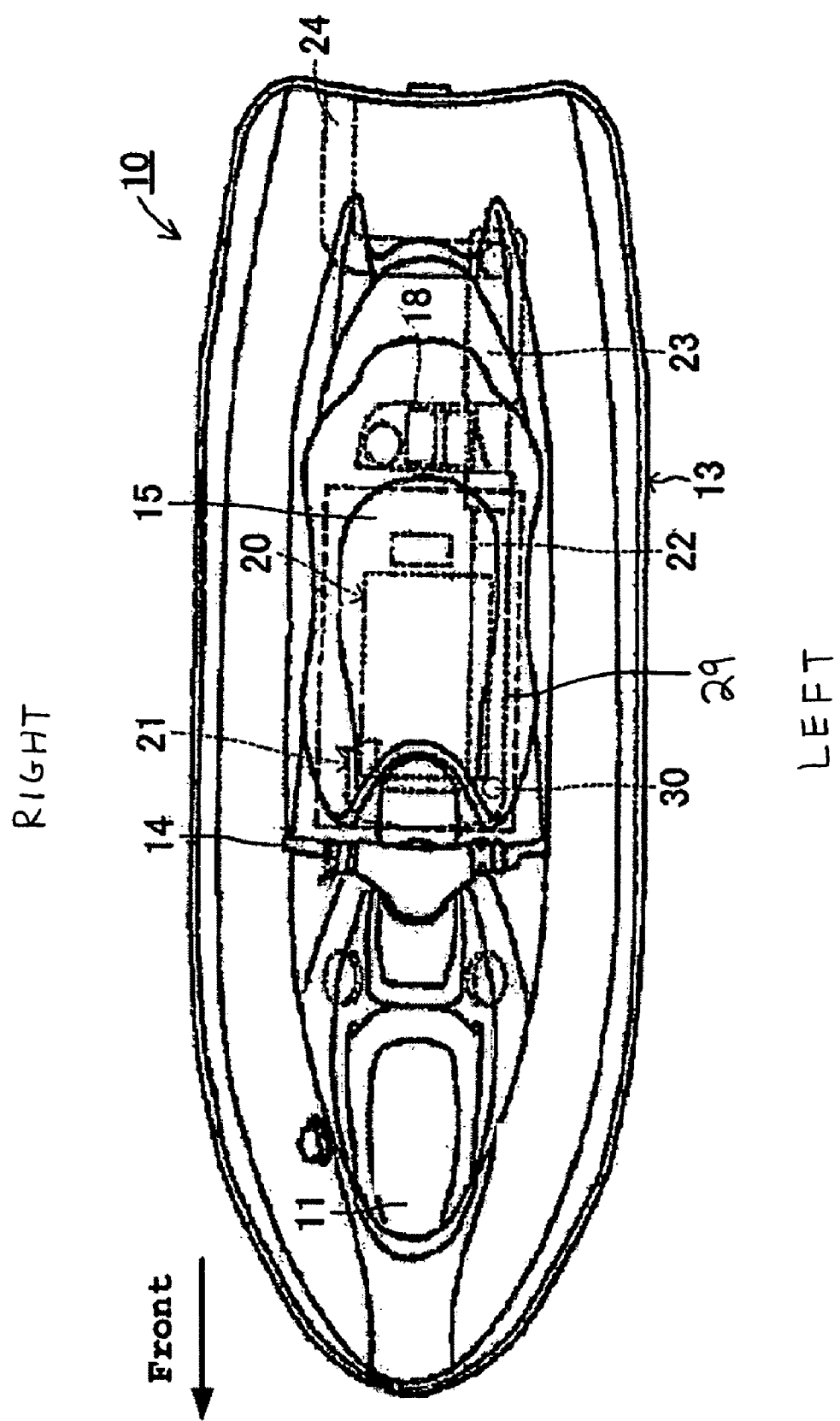
FIG. 2 is a top plan view of the watercraft of FIG. 1.

With reference to FIGS. 1 and 2, an overall configuration of a personal watercraft 10 and its engine 17 and exhaust system 29 is described below. The described exhaust system has particular utility for use with the personal watercraft, and thus, it is described in the context of personal watercraft. However, the exhaust system can also be applied to other types of vehicles, such as small jet boats and other vehicles that feature marine drives, automobiles, motorcycles, scooters, and the like, as well as industrial stationary engines, generators, and other engines, for example. The terms "upper," "lower," "top," "bottom," "left," "right," and the like may be used to describe the watercraft 10. These terms are used in reference to the illustrated embodiments and are from the perspective of a rider straddling a seat 15.

The watercraft 10 has a body 13 that includes upper hull section 11 and a lower hull section 12 (FIG. 1). The upper and lower hull sections 11, 12 cooperate to define an internal cavity that can form an engine compartment. The engine compartment can be defined by a forward and rearward bulkhead; however, other configurations are also possible. The engine compartment is preferably located under the seat 15, but other locations are also possible (e.g., beneath the control mast or the bow).

The watercraft 10 also includes handlebars 14 in front of the seat 15 and on top of the upper hull section 11. The seat 15 is preferably positioned centrally along the upper side of the upper hull section 11. Additionally, foot mounting steps can be formed at the sides of the body 13. Preferably one foot mounting step is on the left side and another foot mounting step is on the right side of the seat 15. The seat 15 has a saddle shape, so that a rider can sit on the seat 15 in a straddle fashion and often is referred to as a straddle-type seat; however, other types of seats can also be employed.

With continued reference to FIG. 1, the fuel tank 16 for storing fuel is disposed in front of the engine 17. Fuel from the fuel tank 16 can be delivered to the engine 17. The engine 17 is a water-cooled, inline four-cylinder, four-cycle engine. The engine 17 has intake valves that are opened and closed for delivering a mixture of fuel and air supplied from the fuel tank 16 and an air intake system 20, respectively. The air intake system 20 is located on the side of the engine 17 and delivers air to the intake valves.

The engine 17 can also have exhaust valves for discharging exhaust gases to the exhaust system 29. An exhaust manifold 21 (FIGS. 2 and 3) is in communication with the exhaust valves. The air-fuel mixture is supplied by the intake valves and is ignited by an ignition device of the engine 17. As such, the ignition device causes explosions that cause vertical reciprocation of the pistons in the engine 17. A crankshaft 17a is rotated by the vertical movement of these pistons.

The illustrated engine merely exemplifies one type of engine which can have an embodiment of the present exhaust system. Engines having a different number of cylinders, other cylinder arrangements, various cylinder orientations (e.g., upright cylinder banks, V-type, and W-type), and operating on various combustion principles (e.g., four stroke, crankcase compression two-stroke, diesel, and rotary) are all practicable for use with the exhaust systems disclosed herein. An exhaust port of each cylinder can be in communication with at least one exhaust passage, such as the exhaust conduit 22 of the exhaust system 29.

With continued reference to FIG. 1, a jet pump unit 18 is driven by the engine 17 to propel the illustrated watercraft 10. The impeller shaft 19 can extend between the crankshaft 17a of the engine 17 and the jet pump unit 18. In the illustrated embodiment, a coupling member is positioned between the impeller shaft 19 and the crankshaft 17a. The crankshaft 17a imparts rotary motion to the impeller shaft 19 which, in turn, drives the pump unit 18.

The jet pump unit 18 is disposed within a tunnel formed on the underside of the lower hull section 12. The jet pump unit 18 preferably comprises a discharge nozzle 18a and a steering nozzle 18b to provide steering action. The steering nozzle 18b is pivotally mounted about a generally vertical steering axis. The jet pump unit 18 can be connected to the handlebars 14 by a cable or other suitable arrangement so that a rider can pivot the steering nozzle 18b for steering the watercraft 10. Other types of marine drives can also be used to propel the watercraft 10 depending upon the application.

The intake system 20 comprises an intake conduit connected to the engine 17 and a throttle valve. The intake system 20 draws in outside air and then supplies the air to the engine 17. The amount of air supplied to the engine 17 can be controlled by the throttle valve. The fuel supplied from the fuel tank 16 by a fuel supply system is mixed with the air from the intake system 20. The mixture is then delivered to the engine 17 for the combustion process.

With respect to FIGS. 1-4, the exhaust system 29 includes an exhaust conduit 22 and an exhaust gas sensor 30. Exhaust gases outputted from the engine 17 pass through the exhaust conduit 22. The exhaust gas sensor 30 is used to analyze the exhaust gases flowing through the exhaust conduit 22. Generally, the exhaust system 29 provides fluid communication between the engine 17 and the external environment. The exhaust system 29 preferably emits exhaust gases, discharged from the engine 17, to an external location at a rear end portion of the body 13.

The upstream end of the exhaust conduit 22 preferably is in communication with the exhaust valves of the engine 17. The exhaust conduit 22 extends from each exhaust valve so that the exhaust gases from the combustion chambers of the engine 17 are mixed within and flow through the exhaust conduit 22.

Figure 3:
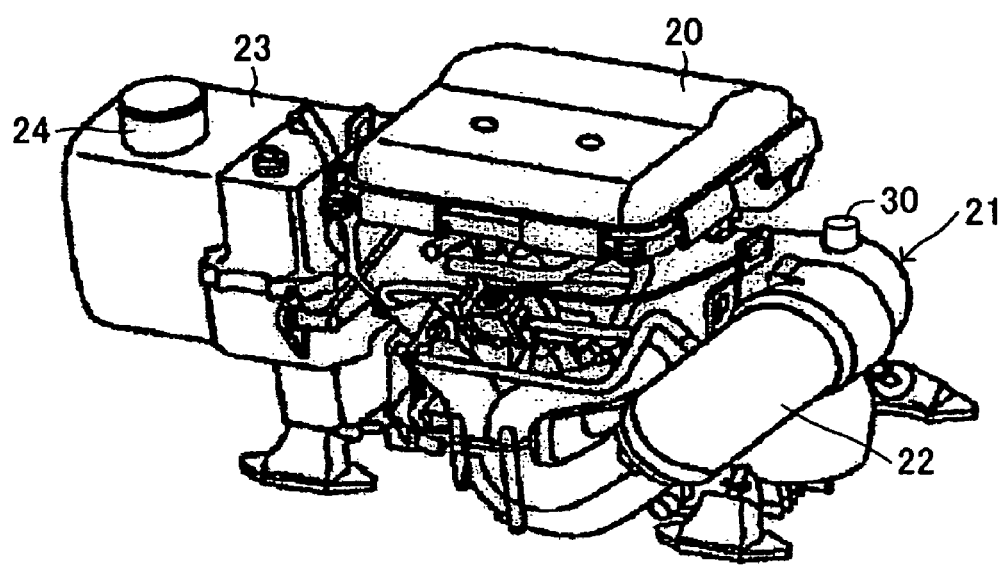
FIG. 3 is a perspective view of an internal combustion engine and an exhaust system of the watercraft of FIG. 1.

The exhaust conduit 22 can be formed of a curve conduit and is in communication with the engine 17, a water-lock 23 connected to the rear end of the exhaust conduit 22, and a water-lock exhaust pipe 24 (FIG. 2). As shown in FIG. 3, the exhaust conduit 22 extends obliquely upward and forward and then curves in front of the engine 17. The exhaust conduit 22 extends generally horizontally in front of the engine 17 and then curves and extends rearwardly on the left side of the engine 17 to the water-lock 23, as shown in FIG. 4.

Figure 4:
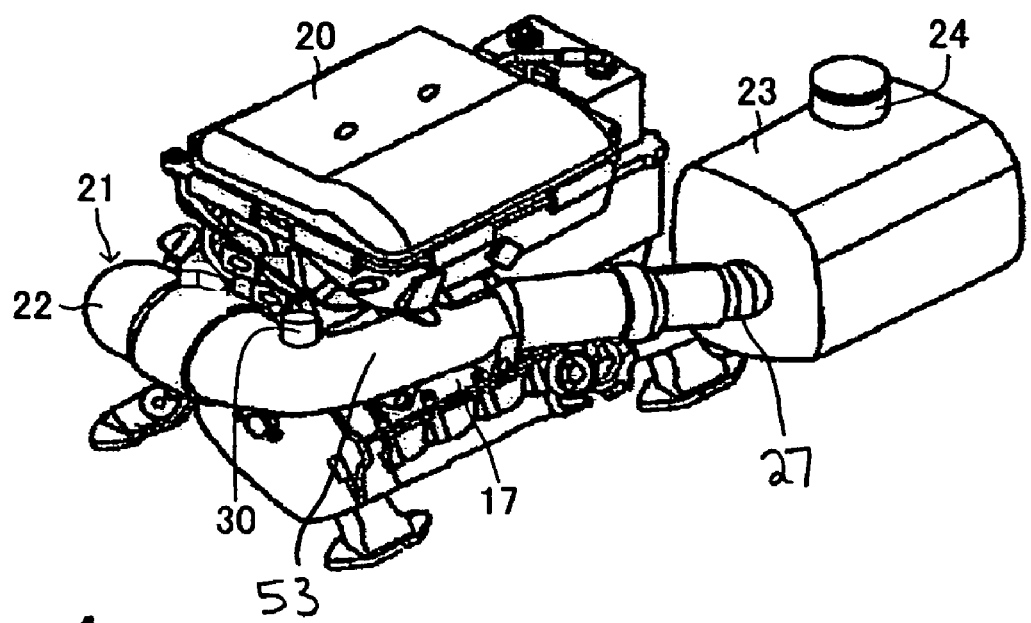
FIG. 4 is another perspective view of the internal combustion engine and the exhaust system of FIG. 3.

The water-lock exhaust pipe 24 is connected to the rear part of the water-lock 23 as shown in FIGS. 2 and 4. The rear end 27 of the exhaust conduit 22 is in communication with a front part of the water-lock 23. Although not illustrated, the exhaust conduit 22 can be connected to an exhaust outlet in the body 13 of the watercraft 10.

The water-lock 23 can be a tank in communication with the exhaust conduit 22. The illustrated water-lock 23 is a generally large-diameter somewhat cylindrical tank. The water-lock 23 can inhibit water from entering and flowing through the exhaust conduit 22 towards the engine 17. The downstream end of the exhaust conduit 22 is connected to front portion of the water-lock 23.

Figure 5:
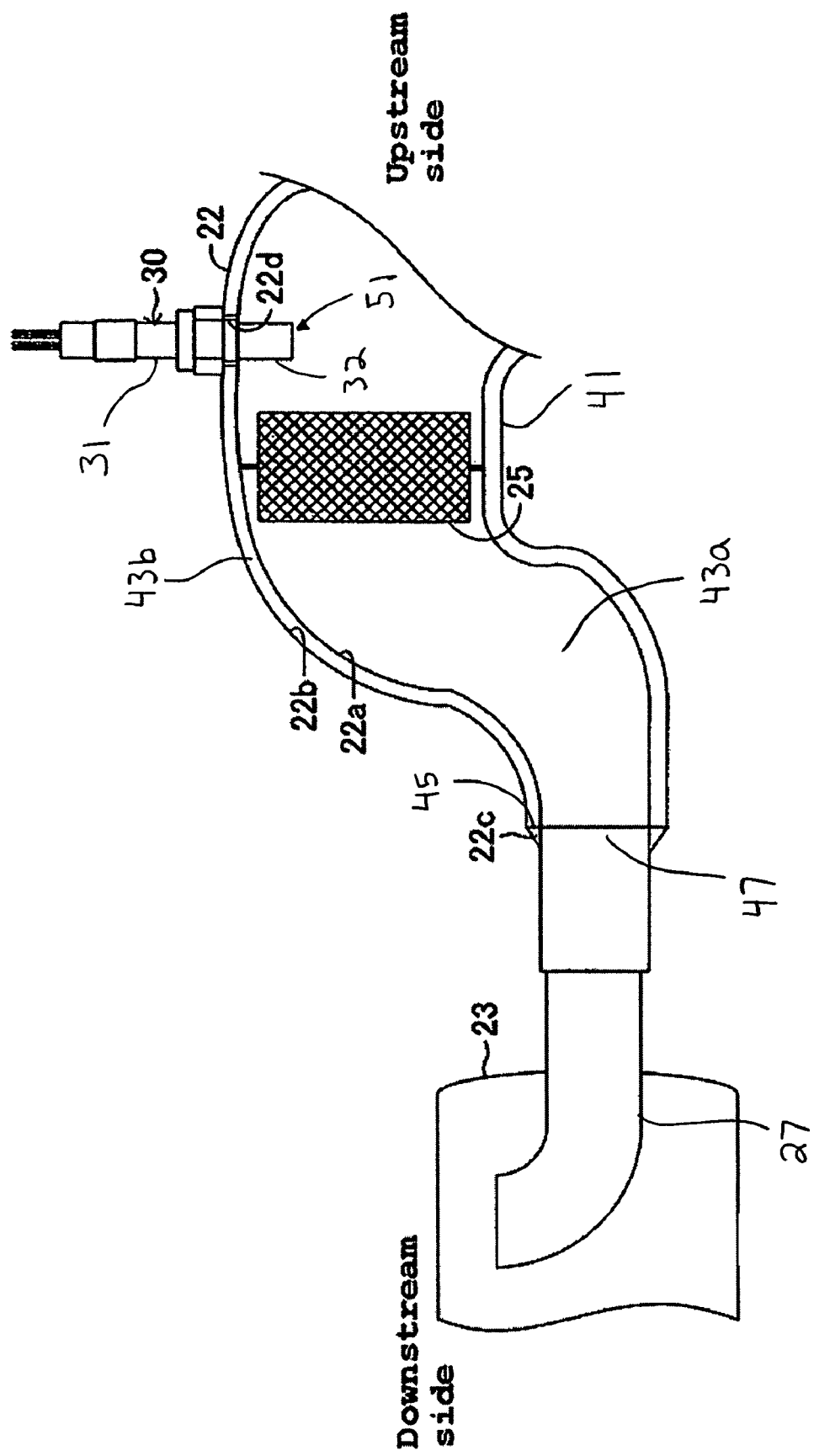
FIG. 5 is a cross-sectional, side elevational view of a portion of the exhaust system of FIG. 1, the exhaust system has an exhaust gas sensor positioned along an exhaust conduit.

With respect to FIG. 5, the exhaust conduit 22 can have a plurality of passageways. The exhaust conduit 22 has an upstream portion 41 that has an inner conduit 22a and an outer conduit 22b that are somewhat concentric. The inner surface of the inner conduit 22a defines an exhaust gas passage 43a. Exhaust gases outputted from the engine 17 can flow through the exhaust gas passage 43a towards the aft end of the watercraft 10.

A cooling water passage 43b is defined by an inner surface of the outer conduit 22b and the outer surface of the inner conduit 22a. Cooling water from a cooling system can flow through the cooling water passage 43b. A cooling water passage outlet 45 of the passage is configured to mix cooling water with exhaust gases flowing through the exhaust gas passage 43a. In the illustrated embodiment, exhaust gases passing through the exhaust gas passage 43a and the cooling water passing through the cooling water passage 43b are mixed with each other at a junction 22c. In some embodiments, the jet pump can be used as a cooling water pump. For example, as is well known in the art, a cooling water passage can extend between the engine, and/or any other component that is to be cooled, to the jet pump. Thus, water that is pressurized by the jet pump can be guided to the engine body and/or other components. The cooling water passage 43b can be part of a closed or open loop system.

The junction 22c is preferably configured to promote mixing of the cooling water and exhaust gases. The illustrated junction 22c includes the cooling water passage outlet 45 and an exhaust gas passage outlet 47. The cooling water passing through the cooling water passage 43b can comprise water that has cooled the engine 17.

For example, cooling water can be passed through one or more cooling water jackets disposed in or on the engine body to cool the engine 17. When the engine 17 operates, the combustion process heats the engine 17. The cooling water, which is cooler than the engine 17, flows through the cooling jackets and absorbs heat from the engine 17 to thereby cool the engine 17. The heated cooling water then passes through the exhaust system 29 and is ultimately emitted outside the watercraft 10.

The cooling water flowing through the cooling water passage 43b may or may not be limited to water that is used to cool the engine 17. For example, water from other portions of the watercraft can be directly sent to the exhaust conduit 22 without passing through the engine 17, or a cooling jacket. Thus, the water passing through the cooling water passage 43b can comprise water that is not used to cool the engine 17.

With continued reference to FIG. 5, the exhaust conduit 22 is configured to direct exhaust gases past the exhaust gas sensor 30. The portion of the exhaust conduit 22 generally extending on the front, left side of the engine 17 has a hole 22d. The exhaust gas sensor 30 is positioned through the hole 22d. In some embodiments, including the illustrated embodiment, the exhaust gas sensor 30 is securely held in the hole 22d and extends into the exhaust gas passage 43a.

The exhaust gas sensor 30 is configured to detect and transmit a signal indicative of one or more constituents (e.g., substances including gases, fluids, and/or particulates) of the exhaust gases discharged from the engine 17. At least a portion of the exhaust gas sensor 30 is disposed in the exhaust gas passage 43a. As such, the exhaust gas sensor 30 is in communication with the exhaust gases flowing through the exhaust conduit 22. A gas detection assembly can extend inwardly into the exhaust gas passage 43b.

Figure 6:
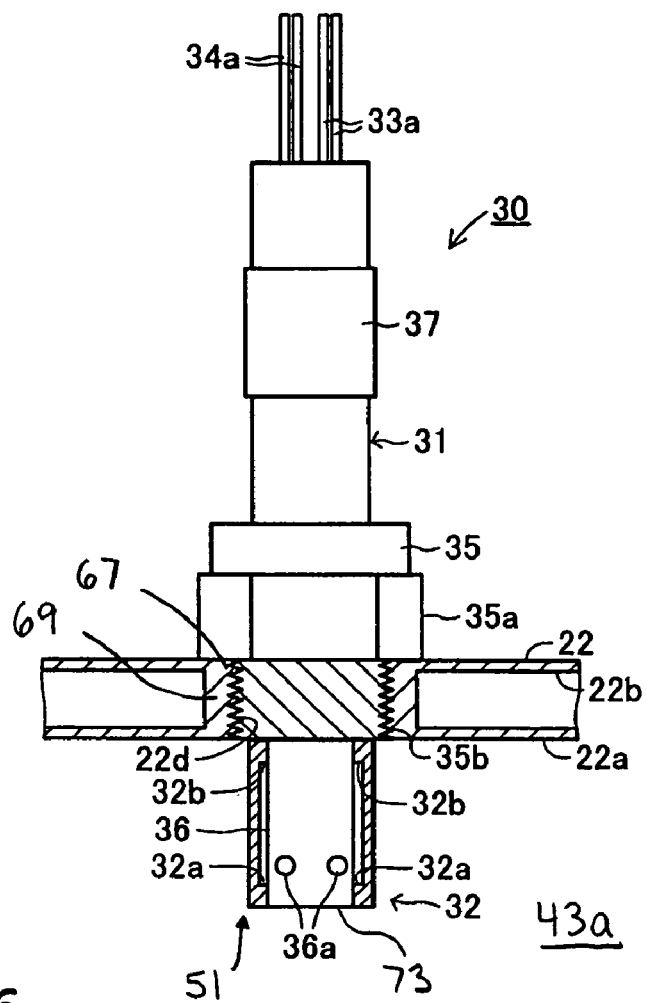
FIG. 6 is a partial cross-sectional, side elevational view the exhaust gas sensor of FIG. 5, the exhaust gas sensor is mounted to the exhaust conduit.

As shown in FIG. 6, the main fitting 35 supports the gas detection assembly 51 and couples the exhaust gas sensor 30 to the hole 22d of the exhaust conduit 22. The detection assembly 51 is supported, at least in part, by the main fitting 35. At least a portion of the main fitting 35 comprises a heat-resistant material, such as heat resistant metals (e.g., steel and its alloys including, but not limited to, stainless steel). In some embodiments, the main fitting 35 is comprised of mostly, or entirely, a heat resistant material. The detection assembly 51 extends through the cylinder bore extending through the main fitting 35.

Figure 7A:
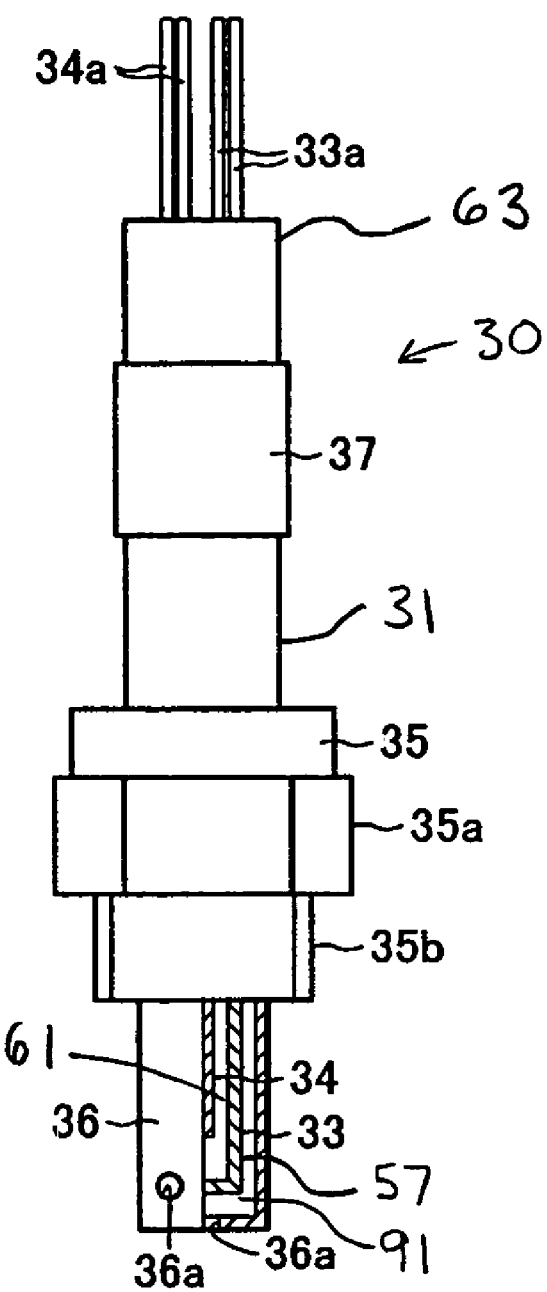
FIG. 7A is a partial cross-sectional, side elevational view of the exhaust gas sensor of FIG. 6, a protective cover has been removed from the exhaust gas sensor.

With reference to FIGS. 6 and 7A, the main fitting 35 preferably has a torque portion 35a adjacent the exhaust conduit 22. The torque portion 35a can have a hexagonal cross-section. In some embodiments, the torque portion 35a can engage a tool for assembling the main fitting 35 and the exhaust conduit 22. Thus, a torque can be easily applied to the main fitting 35. The torque portion 35a can have any configuration including polygonal or non-polygonal configurations.

The threaded portion 35b (see FIG. 6) of the main fitting 35 extends outwardly from the torque portion 35a. The exhaust conduit 22 can have complimentary threads 67 defined by an exhaust conduit mounting portion 69. The exhaust conduit mounting portion 69 forms the hole 22d and extends between the inner conduit 22a and an outer conduit 22b. When the threaded portion 35b is threaded into the exhaust conduit 22, the exhaust gas sensor 30 can be secured to the exhaust conduit 22. The lower end of the torque portion 35a can abut against the outer surface the exhaust conduit 22. In this manner, the exhaust gas sensor 50 can be securely held in the exhaust conduit 22.

Figure 7B:
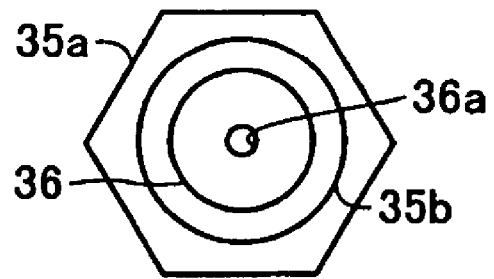
FIG. 7B is a bottom plan view of the exhaust gas sensor of FIG. 7A.

With respect to FIG. 7, the casing 37 can house a joint between a gas detection element 33 and a lead wire 33a and a joint between a heater 34 (e.g., a ceramic heater) and a lead wire 34a. That is, the gas detection element 33 and the ceramic heater 34 can be connected to the lead wires 33a, 34a, respectively, by the casing 37. The casing 37 can be positioned above the main fitting 35 and can comprise a heat resistant material. The casing 37 has a generally cylindrical shape; However, other configurations are possible. The lead wires 33a, 34a extend through a through-hole formed through the upper end of the sensor body 31.

The illustrated exhaust gas sensor 30 has a protective cover 32. As shown in FIG. 7A, the sensor body 31 has a generally cylindrical shape and includes the detection assembly 51 positioned within the exhaust gas passage 43a. The exhaust conduit 22 wall is interposed between a main fitting 35 of the exhaust gas sensor 30 and the detection assembly 51. The casing 37 of the exhaust gas sensor 30 is spaced from the main fitting 35.

With reference to FIGS. 6 and 7A, the detection assembly 51 extends inwardly into the exhaust gas passage 43b and comprises the protective cover 32, an outer housing 36, the detection element 33, and the ceramic heater 34. The detection element 33 is configured to measure one or more constituents in the exhaust gases passing through the exhaust gas passage 43a. The protective cover 32, shown in FIG. 6A but omitted in FIG. 7A, at least partially surrounds the outer housing 36. The outer housing 36 at least partially surrounds the detection element 33. The detection element 33 at least partially surrounds the ceramic heater 34.

In some embodiments, the gas detection element 33 can comprise an electrolyte material that can interact with at least one constituent of the exhaust gas. The gas detection element 33 can generate a voltage in response to at least one constituent of the exhaust gas. The illustrated gas detection element 33 is formed by sintering a solid electrolyte material, such as zirconia, into a closed ended cylindrical shape. As used herein, the term "gas detection element" is to be construed broadly to include, without limitation, oxygen sensors (such as zirconia oxygen sensors, titania oxygen sensors, etc.) or other sensors for measuring at least one substance of the exhaust gas. The gas detection element 33 can comprise one or more of these types of sensors. Additionally, the exhaust gas sensor 33 can also be configured to measure other operating conditions. If the gas detection element 33 is an oxygen sensor, an electric control unit ("ECU") can use a signal (e.g., a signal indicative of the level of oxygen in the exhaust gases) from the exhaust gas sensor 30 to monitor the engine's air/ fuel ratio, thus preventing an excessively lean or rich fuel mixture. The lead wires 33a can be in indirect or direct communication with the ECU.

With continued reference to FIG. 7A, the bottom portion 57 of the gas detection element 33 can be controllably exposed to the exhaust gas. The lead wire 33a is in communication with the gas detection element 33 and extends away from the exhaust gas sensor 30. The lead wire 33a can transmit a signal directly or indirectly to an ECU. The lead wire 33a is preferably connected to the upper end of the detection element 33. A lead wire 34a is configured to supply electric power to the ceramic heater 34. The lead wire 34a is connected to the upper end of the ceramic heater 34 and extends upwardly out of the upper end 63 of the exhaust gas sensor 30.

With continued reference to FIG. 7A, the ceramic heater 34 extends preferably centrally through the detection element 33. The illustrated ceramic heater 34 is positioned near the gas detection element 33. In some embodiments, the ceramic heater 34 is sufficiently close to the gas detection element 33 such that the ceramic heater 34 can effectively control the temperature of the gas detection element 33 when activated. For example, the ceramic heater 34 can be used to heat the gas detection element 33 to a target temperature. As such, the gas detection element 33 can operate at its target temperature for enhanced measuring precision.

The illustrated ceramic heater 34 is a rod-shaped heater for heating the gas detection element 33 in order to maintain the gas detection element 33 at a target temperature, preferably maintaining the gas detection element 33 at a high temperature of about 400° C. to 900° C. The ceramic heater 34 can be any type of heater suitable for heating the gas detection element 33. The illustrated detection assembly 51 has a single ceramic heater 34, but a plurality of ceramic heaters 34 can be employed in alternative embodiments. Non-limiting exemplary heaters can have any suitable type of heating element. The heating elements can comprise ceramic or other material that is heated when a current is applied thereto. Based on the application, a skilled artisan can select a desired heater in view of the present disclosure.

The ceramic heater 34 is housed in a space 61 in the gas detection element 33. The space 61 can be a generally cylindrical space sized to accommodate the gas detection element 33. In such an arrangement, at least a portion of the gas detection element 33 is proximate to, but spaced from, the ceramic heater 34. In some embodiments, the gas detection element 33 and the ceramic heater 34 are generally coaxial, although they can be at other orientations.

The outer housing 36 covers and protects the gas detection element 33 from, e.g., water. As shown in FIG. 7A, the outer housing 36 surrounds the bottom portion 57 of the gas detection element 33 and is attached to the lower end of the main fitting 35. The outer housing 36 provides fluid communication between the exhaust passage 43a and the detection element 33. At least one gas inlet 36a is formed in the outer housing 36. The illustrated outer housing 36 has a plurality of gas inlets 36a for introducing the exhaust gas to the gas detection element 33. Any number of gas inlets 36a can be formed in the outer housing 36 based on the desired fluid flow (e.g., fluid egress and/or ingress) through the outer housing 36.

Figure 6A:
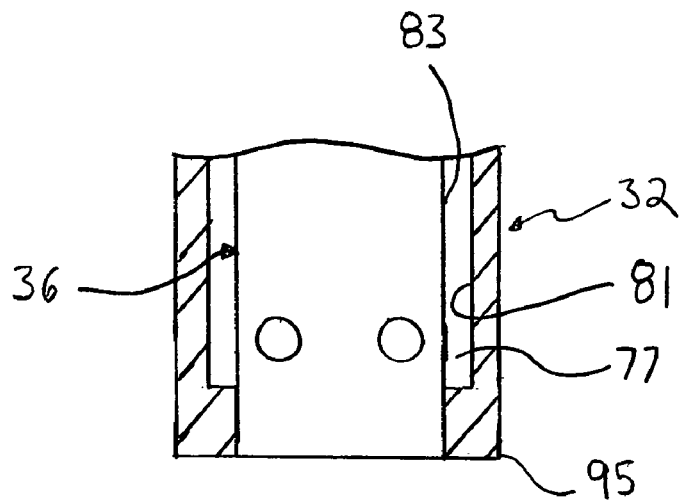
FIG. 6A is an enlarged side elevational view of a bottom end of the exhaust gas sensor of FIG. 6.

With respect to FIGS. 6 and 6A, the inlets 36a can be positioned at any suitable location along the outer housing 36. In some embodiments, the inlets 36a are positioned near the bottom 73 of the outer housing 36. The inlets 36a can be positioned between the lower end 95 of the protective cover 32 and the exhaust conduit 22. For example, the inlets 36a can be spaced from the lower end 95 of the protective cover 32 but are preferably closer to the lower end 95 than the exhaust conduit 22. The outer housing 36 can comprise a heat-resistant metal material and can have a closed-ended cylindrical shape, although the outer housing 36 can have other configurations.

With continued reference to FIG. 6, the protective cover 32 (shown in cross-section) is attached to the outer housing 36 by press-fitting the outer housing 36 into the protective cover 32. However, the protective cover 32 may be attached by other means to the outer housing 36 as long as the protective cover 32 can cover at least a portion of the outer housing 36. The protective cover 32 preferably shields the inlets 36a while permitting some of the exhaust gases to pass through the inlets 36a. For example, the protective cover 32 may be attached to the outer housing 36 by threads, mechanical fasteners, adhesives, welding, or any other suitable coupling means.

Figure 8A:
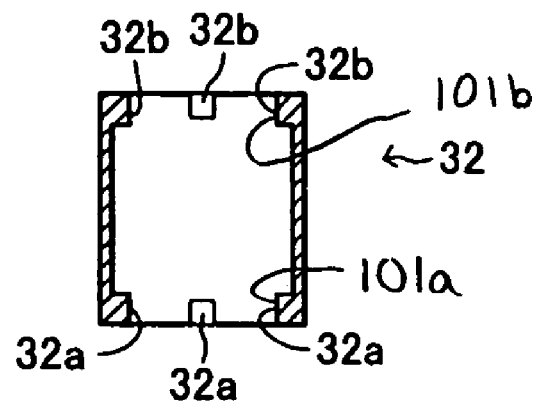
FIG. 8A is a cross-sectional, side elevational view of a protective cover of the exhaust gas sensor.
Figure 8B:
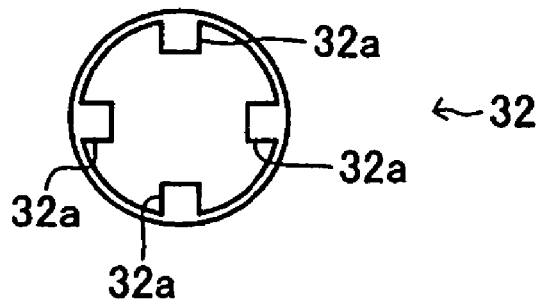
FIG. 8B is a bottom plan view of the protective cover of FIG. 8A.
Figure 8C:
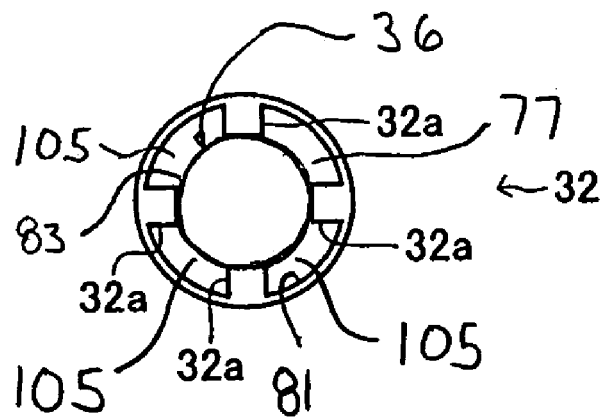
FIG. 8C is a bottom plan view of the protective cover surrounding an outer housing.

The protective cover 32 is sized and configured to cover at least a portion of the outer housing 36. In some embodiments, the protective cover 32 can minimize or limit exposure of the outer housing 36 to, e.g., water or other substances in the exhaust gas passage 43a. The protective cover 32 can comprise a heat resistant material such as stainless steel. The illustrated protective cover 32 has a generally cylindrical shape, as shown in FIGS. 8A-8C. The transverse inner dimension (e.g., the inner diameter) of the protective cover 32 can be greater than the transverse outer dimension of the outer housing 36. As shown in FIGS. 6-8C, the protective cover 32 and the outer housing 36 are generally coaxial.

With reference to FIGS. 6A and 8C, a gas flow passage 77 is defined between the inner surface 81 of the protective cover 32 and the outer surface 83 of the outer housing 36. The illustrated gas flow passage 77 is a generally annular passage, although the gas flow passage 77 can have other configurations suitable for providing fluid communication between the exhaust gas passage 43a and at least one inlet 36a.

In operation, exhaust gases in the exhaust gas passage 43a can flow between the protective cover 32 and the outer housing 36 and into the flow passage 77. The exhaust gases can then flow through the gas flow passage 77 and into at least one of the inlets 36a. In some embodiments, the flow path through the inlets 36a is generally perpendicular to the flow path defined by the flow passage 77 so as to facilitate the removal of one or more substances (e.g., water) from the exhaust gases. That is, one or more substances can be removed from the exhaust gases flowing through gas flow passage 77 into the inlets 36a. The exhaust gases can then fill the space 91 (FIG. 7A) and can be detected by the detection element 33.

With respect to FIG. 7A, the ceramic heater 34 can have an axial length that is equal to or less than the axial length of the detection element 33. The axial length of the detection element 33 can be equal to or less than the axial length of outer housing 36. The axial length of the outer housing 36 can be equal to or less than the axial length of protective cover 32. In some embodiments, including the illustrated embodiment of FIGS. 6 and 6A, the axial length of the protective cover 32 can be generally the same as the axial length of the outer housing 36. In some embodiments, the axial length of the protective cover 32 may be greater than the axial length of the outer housing 36. For example, the protective cover 32 can extend outwardly past the outer housing 36. As such, the bottom 95 of the protective cover 32 can be spaced outwardly from the bottom 76 of the outer housing 36. The length of the protective cover 32 can be increased to further reduce the likelihood that water enters into the detector assembly 51.

With respect to FIGS. 5 and 6, the outer transverse diameter of the protective cover 32 can be smaller than the diameter of the hole 22d in the exhaust conduit 22. As such, the detection assembly 51 can be inserted through the hole 22d and into the exhaust gas passage 43a. To couple the exhaust gas sensor 30 to the exhaust conduit 22, the threaded portion 35b can be rotated and advanced into the hole 22d. Other coupling means can be employed to attach the exhaust gas sensor 30 to the exhaust conduit 22. Non-limiting exemplary coupling means can include, but are not limited to, press-fitting, adhesives, snap fittings, mechanical fasteners, combinations thereof, and the like.

The gas detection assembly 51 can have one or more spacers configured to position the protective cover 32 with respect to the outer housing 36. As used herein, the term "spacer" is to be construed broadly to include, without limitation, a protrusion or other structure that can maintain a desired distance between two components of the detection assembly 51. The spacers can ensure that the gas flow passage 77 is maintained during operation. In some embodiments, including the illustrated embodiment of FIGS. 6A and 8A-8C, the protective cover 32 has four spacers 32a, 32b at either end that can engage the outer housing 36. The spacers 32a can be inwardly extending protrusions formed circumferentially at the lower end 95 of the protective cover 32. In some embodiments, the spacers 32a can be positioned below the inlets 36a. The spacers 32b can be inwardly extending protrusions formed circumferentially at the upper end of the protective cover 32.

The spacers 32a, 32b can be protrusions positioned at generally equal intervals along the lower end 95 of the protective cover 32 and are positioned about the outer housing 36. As shown in FIGS. 8B and 8C, four protrusions 32a can be formed at generally equal intervals forming two pairs of diametrically opposed protrusions 32a. The protrusions 32b can be similarly positioned at the other ends of the protection cover 32.

The protrusions 32a, 32b can be used to attach the protective cover 32 to the outer periphery of the outer housing 36, preferably without closing the gas passage 77 and/or the gas inlets 36a. The end faces 101a, 101b (FIG. 8A) of the protrusions 32a, 32b, respectively, can each have a shape that is generally similar to the shape of at least a portion of the outer housing 36. For example, the end faces 101a, 101b can have an arcuate shape with a radius of curvature which is generally similar to the radius of curvature of the outer surface 83 (FIG. 6A) of the outer housing 36. The inner dimensions defined by the end faces 101a, 101b can be selected to provide a snug fit with the outer housing 36. However, the end faces 101a, 101b can be generally flat, curved, combinations thereof, or have any other configuration suitable for engaging the outer housing 36.

The protrusions 32a, 32b can each have a similar radial length so that the protective cover 32 and the outer housing 36 are generally coaxially. Additionally, a generally uniform gap can be formed between the outer surface 83 of the outer housing 36 and the inner surface 81 of the protective cover 32. As shown in FIG. 8C, a plurality of gaps 105 can be formed between the protective cover 32 and the outer housing 36. The gaps 105 can form openings to the gas passage 77.

To assemble the sensor body 31 and the protective cover 32, the outer housing 36 can be inserted into the protective cover 32. The bottom 73 of the outer housing 36 can be inserted between the protrusions 32b and advance into the protective cover 32. The protective cover 32 can be slid over the outer housing 36 until the protective cover 32 surrounds the outer housing 36 as desired. In some embodiments, the outer housing 36 is slid into the protective cover 32 until the lower end of the threaded portion 35b of the main fitting 35 abuts against the upper end of the protective cover 32. As such, the protrusions 32b are adjacent the lower surface of the threaded portion 35b. The protrusions 32a, 32b can surround the bottom 73 and top, respectively, of the outer housing 36.

If the protrusions 32a, 32b provide a somewhat tight fit with the outer housing 36, the outer housing 36 can be press-fitted into the protective cover 32. The protective cover 32 can then be fixedly attached to the outer periphery of the outer housing 36. When the protective cover 32 is attached to the outer housing 36, the gaps 105 can have a width equal to the length of the protrusions 32a, 32b.

The protective cover 32 can be attached to the outer housing 36 by any means as long as the protective cover 32 permits fluid communication between the gas inlets 36a and the exhaust gas passage 43a. For example, one, two, three, or more protrusions 32a and one, two, three, or more protrusions 32b may be formed on the inner periphery of the protective cover 32. In some non-limiting exemplary embodiments, five or more protrusions 32a and 32b are provided. The protrusions 32a and 32b are not necessarily formed at opposing ends of the protective cover 32. For example, the protrusions 32a and 32b may be spaced from the upper and lower ends of the protective cover 32. Protrusions with the same shape as the protrusions 32a and 32b, may be provided only at an intermediate portion in the axial direction of the inner periphery of the protective cover 32.

The assembled exhaust gas sensor 30 is mounted to the exhaust conduit 22, as shown in FIG. 6. The gas detection element 33 can extend through the exhaust conduit 22b and can be located in the exhaust passage 43a. In some embodiments, the exhaust gas sensor 30 is positioned upstream of a catalyst 25 located in the exhaust conduit 22, as shown in FIG. 5. In such an arrangement, the exhaust gas sensor 30 can detect the concentration of oxygen in the exhaust gas before the exhaust gas is introduced into the catalyst 25. The exhaust gas sensor 30 is attached to the upper wall of the exhaust conduit 22. This is to prevent the exhaust gas sensor 30 from being exposed to water, even if water flows upstream along the exhaust conduit 22 towards the engine 17. If water flows upstream along the exhaust conduit 22, the water can pass below the exhaust gas sensor 30.

The exhaust gas sensor 30 can also be mounted at other locations in the exhaust system. In some embodiments, the exhaust gas sensor 30 can be positioned downstream of the catalyst 25. The exhaust gas sensor 30 can be installed at any position along passage in which exhaust gas discharged from the cylinder of the engine 17 flows. For example, the exhaust gas sensor 30 may be installed in a position close to the upstream end of the exhaust conduit 22, or in an exhaust gas passage in communication with one of the cylinders of the engine 17. In some embodiments, the sensor can be positioned downstream of the catalyst 25. The sensor can also be used for a different purpose than the sensor 30 disclosed above.

The illustrated catalyst 25 is positioned in the exhaust gas passage 43a so that exhaust gases pass through the catalyst 25 before mixing with the cooling water. The catalyst 25 can remove combustion byproducts and/or unburned hydrocarbons from the exhaust gases and is positioned upstream of the water-lock 23. As such, the cooling water may not contact and impair the performance of the catalyst 25 during normal operating conditions.

In some embodiments, the catalyst 25 has a honeycomb base material that is coated with platinum. However, other configurations and types of catalyst or catalytic converters can be used to remove combustion by-products and/or other substances from the exhaust gases.

When the rider of the watercraft 10 sits on the seat 15 and turns on the start switch, the watercraft 10 can be in a drivable state. When the rider operates the steering handlebar 14 and a throttle operator provided on the steering handlebar 14, the watercraft 10 travels in a direction and at a speed in accordance with the operation.

Exhaust gas outputted from the engine 17 flows through the exhaust conduit 22 towards the water-lock 23. Some of the exhaust gas flowing through the exhaust passage 43a flows into the detection assembly 51. The detection assembly 51 then analyzes the exhaust gases contained therein.

In some embodiments, the exhaust gas flows into the detection assembly 51 by flowing vertically through the gaps 105 and along the passage 77. The exhaust gas proceeds along the passage 77 and eventually inwardly through the gas inlets 36a into the space 91. The detection element 33 can measure the amount or concentration of oxygen in the exhaust gases in the space 91. In this manner, exhaust gases can be continuously or discontinuously delivered to the detection element 33, as desired. During that time, the gas detection element 33 detects the levels of oxygen and sends a detection value to the ECU. The air-fuel ratio of the air-fuel mixture supplied to the engine 17 is controlled by the ECU based on the detection value.

When the detection assembly 51 operates, the gas detection element 33 can be maintained at a target temperature, or within a target temperature operating range. The ceramic heater 34 can be used to control the temperature of the detection element 33 as desired. Such ceramic heater 34 can be utilized to ensure that the detection element 33 is maintained at a high temperature. For example, the detection element 33 can be maintained at a temperature in the range of about 400° C. to 900° C. In some embodiments, the outer housing 36 and the protective cover 32 are also maintained at the high temperature.

Cooling water flowing through the cooling water passage 22b can be converted into mist when injected through the junction 22c into the exhaust passage 43a and mixed with the exhaust gas. For example, the exhaust gases passing through exhaust passage 43a heats and may vaporize at least a portion of the cooling water passing out of the outlet 45. The mixing of the hot exhaust gases and the cooling water may, in some instances, cause mist to form in the exhaust system 29.

Pulsations of the exhaust gas may cause the exhaust gas/cooling water mixture to flow upstream along the exhaust conduit 22. The protective cover 32 covers the outer housing 36 and limits or prevents the expose of the outer housing 36 to water (including mist) in the exhaust gases. Even if water drops contact the protective cover 32, the water drops are quickly evaporated as the protective cover 32 is maintained at a high temperature. Thus, cooling water does not collect on the protective cover 32. The detection assembly 51 can be maintained at a suitable temperature to prevent precipitation of water in the exhaust gas thereby preventing damage to the gas detection element 33.

The pulsation of the exhaust gases in the exhaust gas conduit 22 can cause exhaust gases to flow into and out of the detection assembly 51. During normal engine operation, for example, pressure pulses of the exhaust gases in the exhaust conduit 22 can cause the exhaust gases to flow in and out of the detection assembly 51.

The exhaust gases can be expelled out of the detector assembly 51. The circulating exhaust gases within the chamber 91 can be discharged through the inlets 36a. The exhaust gases then proceed downwardly through the gas passage 77 and out of the gaps 105. In this manner, the exhaust gases are expelled from the detection assembly 51.

When the watercraft 10 is maneuvered, outside water may flow in reverse from downstream to upstream through the water-lock exhaust pipe 24 and may reach the upstream side of the exhaust conduit 22 beyond the water-lock 23. However, because the outer periphery of the outer housing 36 is covered with the protective cover 32, the outer periphery of the outer housing 36 is not exposed to water. Also, even if water drops adhere to the protective cover 32, they are immediately evaporated since the protective cover 32 is maintained at a high temperature. Thus, the water does not enter the inside of the protective cover 32. The gas detection element 33 is thereby prevented from being damaged. Even if the protective cover 32 gets wet with water, exhaust gas can be introduced to the gas detection element 33 housed in the outer housing 36 through the gaps 105 and the gas inlets 36a.

The protective cover 32 can be formed of a high heat resistance and high corrosion resistance material, such as stainless steel. The protective cover 32 can effectively prevent the outer housing 36 from being exposed to water and/or generating heat to evaporate water. In some embodiments, the protective cover 32 has a relatively high thickness so that it has a large heat storage capacity.

The protective cover 32, the outer housing 36, and the gas detection element 33 are generally not exposed to water, thus prolonging the life of the exhaust gas sensor 30. Additionally, a rapid decrease of the temperature of the gas detection element 33 can be prevented, thereby minimizing any decrease in the accuracy of the measurements taken by the exhaust gas sensor 30.

Because the gaps 105 have a width equal to the length of the protrusions 32a and 32b, exhaust gases flowing through the exhaust passage 43a of the exhaust conduit 22 flow into the outer housing 36 through the gaps 105 and the gas inlets 36a. As such, exhaust gases can be reliably introduced to the gas detection element 33, and the exhaust gas detection accuracy can be maintained at a high level.

The illustrated outer diameter of the protective cover 32 is generally the same as that of the threaded portion 35b of the main fitting 35. However, the outer diameter of the protective cover 32 may be greater than that of the threaded portion 35b. In such an arrangement, the thickness of the protective cover 32 is increased for an increased heat storage capacity and a higher heat-retaining property of the protective cover 32. Then, even when the protective cover 32 gets wet with water repeatedly, the water on the protective cover 32 can be immediately evaporated and a decrease in temperature of the gas sensor 30, including the outer housing 36 and the gas detection element 33, can be minimized.

Figure 9:
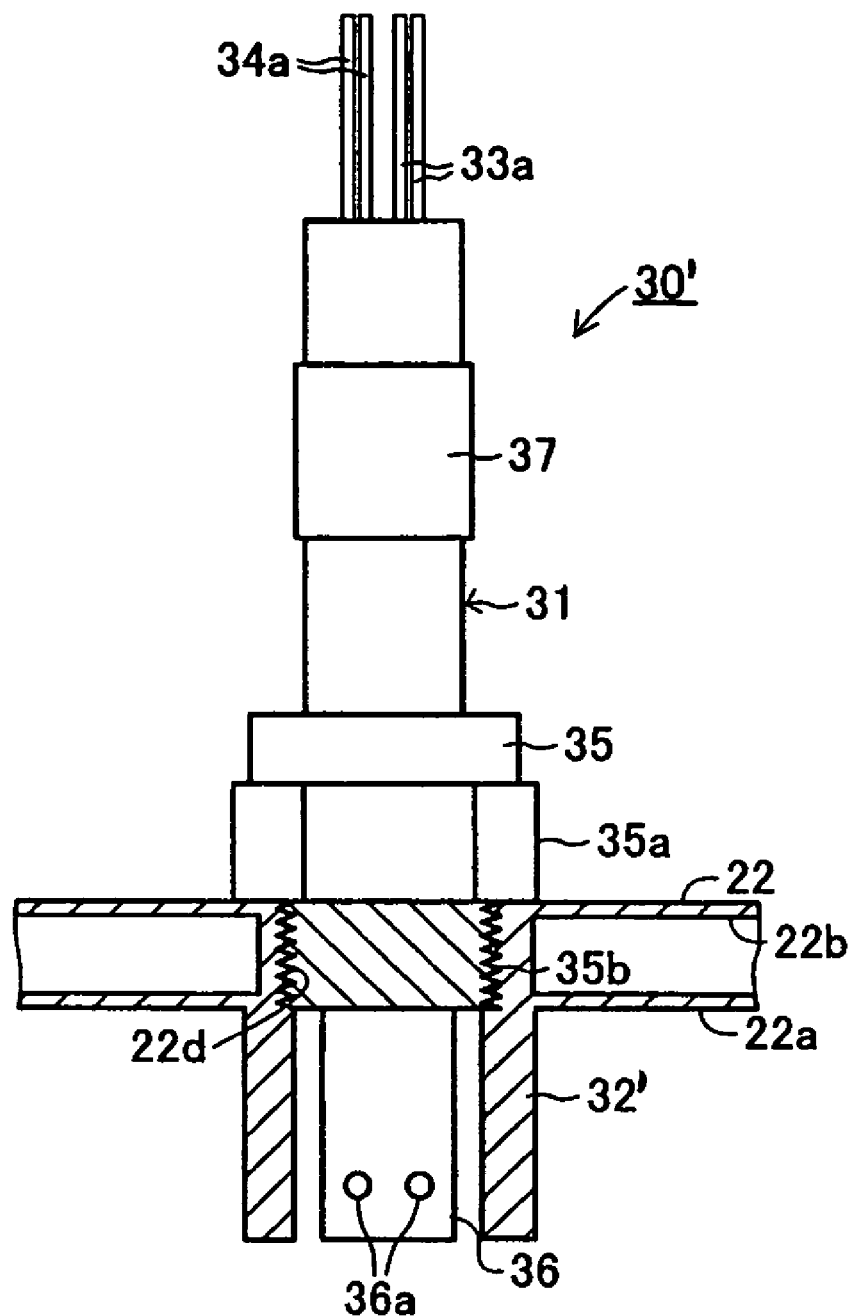
FIG. 9 is a partial cross-sectional, side elevational view of another embodiment of an exhaust gas sensor mounted to an exhaust conduit.

FIG. 9 illustrates another embodiment of an exhaust gas sensor. The illustrated exhaust gas sensor 30' can be generally similar to the exhaust gas sensor 30 and, accordingly, the description of the exhaust gas sensor 30 applies equally to the exhaust gas sensor 30', unless indicated otherwise. Similar elements are identified with identical reference numerals in the depiction of the embodiments of FIGS. 1-8C.

In some embodiments, the protective cover 32' is provided on the inner surface of the exhaust passage 43a. The protective cover 32' can be coupled directly to the exhaust conduit 22. In the illustrated embodiment, the protective cover 32' is integrally formed with the exhaust conduit 22. Alternatively, the protective cover 32' and the exhaust conduit 22 can have a multi-piece construction. For example, the protective cover 32' can be coupled to the exhaust conduit 22 by, for example, threads, mechanical fasteners, press-fitting, and the like. Alternatively, the protective cover 32' can be attached to the sensor body 31. For example, the protective cover 32' can be attached to the main fitting 35 by, for example, threads, mechanical fasteners, press-fitting, and the like.

The inner periphery of the hole 22*d* of the exhaust conduit 22 can extended inwardly to form a generally cylindrical protective cover 32'. The outer and inner diameters of the protective cover 32' may or may not be the same as the outer and inner diameters of the protective cover 32' described above. The protective cover 32' can be spaced from the outer housing 36 without utilizing spacers, such as the protrusions 32*a* and 32*b* described above.

When the exhaust gas sensor 30' is attached to the exhaust conduit 22, the outer housing 36 is inserted into the hole 22*d* and the threaded portion 35*b* of the exhaust gas sensor 30' is threaded into the hole 22*d*. The outer housing 36 of the exhaust gas sensor 30' is thereby located inside the protective cover 32'.

Although the exhaust gas sensors described above can detect the concentration of oxygen in exhaust gas, the exhaust gas sensors can be used to detect other component(s) of exhaust gases. In some embodiments, the exhaust gas sensors can be configured to detect an amount of substances, such as carbon oxide (CO), hydrocarbons (HC), and nitrogen oxides (NOx). Thus, exhaust gas sensors can be HC sensor or a NOx sensor which are used to measure constituents of an exhaust gas.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. An exhaust gas sensor for an exhaust system, the exhaust sensor comprising:
    a gas detection element configured to detect an amount of a substance in a gas,
    an outer housing including a sidewall and a bottom wall, the sidewall of the outer housing including a plurality of gas inlets arranged to provide fluid communication through the outer housing, the gas detection element positioned within the outer housing,
    a main fitting arranged to directly support a gas detection assembly including the gas detection element and the outer housing, and
    a protective cover arranged to cover and surround the outer housing, the protective cover comprising a side wall and a lower end, the lower end not substantially overlying the bottom wall of the outer housing and the side wall not comprising openings in proximity to the plurality of gas inlets but the gas inlets communicating with locations outside of the protective cover adjacent the bottom wall of the outer housing, the protective cover further comprising a cylindrical body with an inner periphery on which a plurality of protrusions are arranged circumferentially at substantially equal intervals, the plurality of protrusions being arranged to press-fit the protective cover onto the outer housing, some of the plurality of protrusions being disposed at a first portion of the protective cover and the remainder of the plurality of protrusions being disposed at a second portion of the protective cover, the first portion and the second portion of the protective cover being spaced apart from each other in an axial direction of the protective cover; wherein
    the protective cover is arranged to slide onto the outer housing such that an uppermost end of the protective cover is arranged below a lowermost end of the main fitting.

2. The exhaust gas sensor of claim 1, wherein at least one gap is formed between the protective cover and the outer housing.

3. The exhaust gas sensor of claim 1, wherein the protective cover is made of stainless steel.

4. An exhaust system for a watercraft having an engine, the exhaust system comprising:
    an exhaust conduit, the exhaust conduit including an exhaust gas passage through which exhaust gases discharged from the engine pass,
    an exhaust sensor comprising a gas detection assembly disposed in the exhaust gas passage and exposed to exhaust gases, the gas detection assembly comprising a gas detection element configured to detect an amount of a substance in exhaust gases,
    an outer housing arranged to surround the gas detection element and including at least one gas inlet arranged to provide fluid communication through the outer housing,
    a main fitting arranged to directly support the gas detection assembly, and
    a protective cover comprising a sidewall that substantially surrounds an outer side surface of the outer housing and the sidewall not comprising openings that extend generally perpendicular to the outer side surface of the outer housing, the protective cover further comprising an elongated body that includes a plurality of inwardly extending spacers, the plurality of inwardly extending spacers are spaced circumferentially along an inner surface of the elongated body and arranged to press-fit the protective cover onto the outer housing, a first plurality of inwardly extending spacers being disposed at a first portion of the protective cover and a second plurality of inwardly extending spacers being disposed at a second portion of the protective cover, the first portion and the second portion of the protective cover being spaced apart from each other in an axial direction of the protective cover; wherein
    the protective cover is arranged to slide onto the outer housing such that an uppermost end of the protective cover is arranged below a lowermost end of the main fitting.

5. The exhaust system of claim 4, further comprising a gas chamber defined by the gas detection element and the outer housing, the gas chamber being in fluid communication with the at least one gas inlet.

6. The exhaust system of claim 4, further comprising a gas passage defined between the outer housing and the protective cover and extending between the at least one gas inlet and the exhaust gas passage of the exhaust conduit.

7. The exhaust system of claim 4, further comprising at least one gap defined between the outer housing and the protective cover, the at least one gap is in fluid communication with the at least one gas inlet.

8. The exhaust system of 7, wherein the at least one gap is positioned such that exhaust gases pass through the at least one gap before entering the at least one gas inlet, and the at least one gap is formed by the spacers and the outer housing and the protective cover.

9. The exhaust system of claim 4, wherein the protective cover comprises stainless steel.

10. The exhaust system of claim 4, wherein the protective cover is disposed so as to shield the at least one gas inlet of the outer housing.

11. The exhaust system of claim 4, wherein the exhaust gas sensor is mounted to the exhaust conduit and is positioned between a water-lock and the engine.

12. An exhaust system for a watercraft having an engine, the exhaust system comprising:
   an exhaust conduit, the exhaust conduit including an exhaust gas passage through which exhaust gases discharged from the engine pass,
   an exhaust sensor comprising a gas detection assembly disposed in the exhaust gas passage and exposed to exhaust gases, the gas detection assembly comprising a gas detection element configured to detect an amount of a substance in exhaust gases,
   an outer housing arranged to surround the gas detection element and including at least one gas inlet arranged to provide fluid communication through the outer housing,
   a main fitting arranged to directly support the gas detection assembly, and
   a protective cover substantially surrounding an outer side surface of the outer housing, the protective cover comprising a sleeve-like member that is spaced apart from the outer side surface of the outer housing, a lower end of the protective cover and a lower end of the outer housing defining a generally annular opening with first protrusions that extend between a lower portion of the protective cover and a lower portion of the outer housing interrupting the generally annular opening and second protrusions that extend between an upper portion of the protective cover and an upper portion of the outer housing interrupting the general annular opening, the lower portion of the protective cover being spaced apart from the upper portion of the protective cover in an axial direction of the protective cover; wherein
   an inner surface of the protective cover is press-fit onto an outer surface of the outer housing via the first and second protrusions; and
   the protective cover is arranged to slide onto the outer housing such that an uppermost end of the protective cover is arranged below a lowermost end of the main fitting.

13. The exhaust system of claim 12, wherein the outer housing has at least one opening inlet defining the at least one fluid passage.

14. The exhaust system of claim 13, wherein the at least one opening inlet is positioned between opposing ends of the protective cover.

15. The exhaust system of claim 12, wherein a heater is positioned within the gas detection element, and the heater is adapted to heat the gas detection element to a target temperature for operating the detection element.

16. The exhaust system of claim 12, wherein the gas detection element is an oxygen sensor.

17. The exhaust gas sensor of claim 1, wherein the gas inlets communicate with locations outside of the protective cover through at least one gap that comprises an annular gap.

18. The exhaust gas sensor of claim 1, wherein the sidewall of the protective cover does not have any holes for receiving exhaust gas therethrough.

19. The exhaust system of claim 4, wherein the exhaust sensor is disposed upstream of a catalyst in the exhaust gas passage.

20. The exhaust system of claim 4, wherein the protective cover is not coupled to the exhaust conduit.

21. The exhaust gas sensor of claim 2, further comprising a fluid passage in which exhaust gases flow through, the fluid passage is defined between the outer housing and the protective cover and extends between the at least one gap and at least one of the plurality of gas inlets of the outer housing.

22. An exhaust gas sensor for an exhaust system, the exhaust sensor comprising:
   a gas detection element configured to detect an amount of a substance in a gas,
   an outer housing including a sidewall and a bottom wall, the sidewall of the outer housing including a plurality of gas inlets arranged to provide fluid communication through the outer housing, the gas detection element positioned within the outer housing,
   a main fitting arranged to directly support a gas detection assembly including the gas detection element and the outer housing, and
   a protective cover arranged to cover and surround the outer housing, the protective cover comprising a sidewall and a lower end, protrusions extending between the sidewall of the protective cover and the sidewall of the outer housing to press-fit the protective cover onto the outer housing, gaps between adjacent ones of the protrusions defining openings from outside of the protective cover into a space defined between the sidewall of the protective cover and the sidewall of the outer housing, and the openings not extending through the sidewall of the protective cover, some of the protrusions being disposed at a first portion of the protective cover and the remainder of the protrusions being disposed at a second portion of the protective cover, the first portion and the second portions of the protective cover being spaced apart from each other in an axial direction of the protective cover; wherein
   the protective cover is arranged to slide onto the outer housing such that an uppermost end of the protective cover is arranged below a lowermost end of the main fitting.

* * * * *